US009149548B2

(12) United States Patent　　(10) Patent No.: US 9,149,548 B2
Davis　　(45) Date of Patent: Oct. 6, 2015

(54) MOBILE UV STERILIZATION UNIT WITH SEPARABLE STERILIZATION MODULE

(75) Inventor: Michael E. Davis, Indianapolis, IN (US)

(73) Assignee: GreenZapr, Inc., Indianapolis, IN (US)

( * ) Notice: Subject to any disclaimer, the term of this patent is extended or adjusted under 35 U.S.C. 154(b) by 776 days.

(21) Appl. No.: 13/417,610

(22) Filed: Mar. 12, 2012

(65) Prior Publication Data

US 2012/0168647 A1　　Jul. 5, 2012

Related U.S. Application Data

(63) Continuation-in-part of application No. 12/966,232, filed on Dec. 13, 2010, now Pat. No. 8,747,770, which is a continuation-in-part of application No. 12/775,515, filed on May 7, 2010, now Pat. No. 8,506,897.

(51) Int. Cl.
*A61N 5/00* (2006.01)
*B01J 19/00* (2006.01)
*A61L 2/10* (2006.01)
*A61L 2/00* (2006.01)

(52) U.S. Cl.
CPC .............. *A61L 2/10* (2013.01); *A61L 2202/14* (2013.01); *A61L 2202/16* (2013.01)

(58) Field of Classification Search
CPC .............................. A61L 2/10; A61L 2202/16
USPC ................................ 422/24, 291; 250/492.1
See application file for complete search history.

(56) References Cited

U.S. PATENT DOCUMENTS

| | | | |
|---|---|---|---|
| 3,633,679 A | 1/1972 | Dahlberg et al. | |
| 5,902,552 A | 5/1999 | Brickley | |
| 5,968,455 A | 10/1999 | Brickley | |
| 7,459,694 B2 | 12/2008 | Scheir et al. | |
| 2002/0139355 A1 | 10/2002 | Gracyalny et al. | |
| 2003/0159840 A1 | 8/2003 | Schmidt | |
| 2005/0022844 A1* | 2/2005 | Field et al. | 134/6 |
| 2007/0192986 A1* | 8/2007 | Garcia et al. | 15/339 |
| 2008/0295271 A1 | 12/2008 | Perunicic | |
| 2010/0104471 A1 | 4/2010 | Harmon et al. | |
| 2011/0214686 A1* | 9/2011 | Chavana et al. | 134/1 |

FOREIGN PATENT DOCUMENTS

| | | |
|---|---|---|
| JP | 09239352 A | 9/1997 |
| KR | 20-0170293 | 2/2000 |
| KR | 20-0353596 | 6/2004 |
| KR | 20-0380226 | 3/2005 |
| KR | 10-0518620 | 10/2005 |
| KR | 20-0407560 | 1/2006 |

OTHER PUBLICATIONS

International Search Report—PCT/US2011/033089—KR 20-0380226—Figs. 2-4.

* cited by examiner

*Primary Examiner* — Kevin Joyner
(74) *Attorney, Agent, or Firm* — Woodard, Emhardt, Moriarty, McNett & Henry LLP

(57) ABSTRACT

A UV sterilization unit. A plurality of UV lamps are removably mounted to a portable lamp housing. The portable lamp housing is mounted to a wheeled vehicle and may be used to destroy infectious material located beneath or remotely from the vehicle.

12 Claims, 18 Drawing Sheets

MOBILE UV STERILIZATION UNIT WITH SEPARABLE STERILIZATION MODULE

This application is a continuation-in-part of U.S. patent application Ser. No. 12/966,232, filed Dec. 13, 2010, now U.S. Pat. No. 8,747,770, which is a continuation-in-part of U.S. patent application Ser. No. 12/775,515, filed May 7, 2010, now U.S. Pat. No. 8,506,897, both of which are hereby incorporated by reference.

BACKGROUND OF THE INVENTION

1. Field of the Invention

The present invention is in the field of apparatus for sterilizing fields and more specifically sports fields.

2. Description of the Prior Art

High-performance, artificial athletic fields are increasingly being installed and used in communities. Many of these fields are "infill turf systems" in which blades of synthetic grass are tucked into a backing system that is covered with a deep layer of sand and/or synthetic particles (the infill material). The infill materials are often made of small particles of rubber or plastic, which fills the spaces between the fibers (blades of "grass") to hold the fibers up and to provide a cushion surface.

The infill material and synthetic fibers can provide a host for a variety of substances including mold, bacteria and a variety of germicidal agents. The current procedure is to spray various chemicals on the field to thereby sterilize the field and provide a safe environment. Spraying of chemicals onto artificial fields is quite expensive due not only to the labor involved but also the cost of raw materials.

An alternate approach in decontaminating surfaces is through the use of ultraviolet light. For example, In U.S. Pat. No. 7,459,694, there is disclosed a mobile germicidal system for decontaminating walls and a ceiling of a room. Germicidal lamps are positioned adjacent the wall and/or ceiling to thereby sterilize the surface. U.S. Pat. No. 5,902,552 discloses an ultraviolet air sterilization device for connection to an air handling duct for the purpose of sterilizing the air as it flows through the duct. U.S. Pat. No. 5,968,455 discloses a mobile unit incorporating many of the features of U.S. Pat. No. 5,902,552 and includes a wheeled carriage with a handle to allow the operator to traverse the sterilization device over a floor covering.

In my aforementioned parent U.S. patent applications, I have disclosed a mobile device that is easily movable across a field such as a synthetic soccer or football field while quickly destroying undesirable agents existing on the synthetic field. In many cases, the fields will have goal post, benches, and other objects located on or adjacent the field. The mobile device disclosed in my aforementioned parent U.S. patent applications, are sized such that it is difficult to sanitize the turf immediately adjacent the objects. I have therefore provided and disclosed herein a smaller mobile device that has ultraviolet lights for destroying all undesirable foreign materials on the turn immediately adjacent the objects.

In many cases, it is desirable to sanitize interior spaces of buildings including locker rooms, weight rooms and fitness areas. I have therefore provided a sterilization module carried on but separable from the mobile UV sterilization unit. The sterilization module includes the same germicidal UV technology as the mobile UV sterilization unit and can be powered by an onboard generator or plugged into any electric wall outlet via a power cord. Thus, lockers, benches, etc. within the interior spaced may be sanitized.

SUMMARY OF THE INVENTION

One embodiment of the present invention is a mobile UV Sterilization Unit connectable to an internally generated source of electrical energy and an externally generated source of electrical energy to destroy infectious material located on a surface and comprises a wheeled carriage having a frame with wheels depending therefrom and a device attached thereto to guide the carriage across a surface. A first portable lamp module has a first position removably located on the frame when the carriage is moved across a surface to be sterilized and a second position located remotely from the frame when the surface to be sterilized is located remotely from the carriage. The module has a lamp housing with an housing open bottom. A first set of ultraviolet lamps is removably mountable in the lamp housing and is positioned to shine downwardly through the open bottom of the housing to shine against a surface to be sterilized. The lamps have proximal ends and distal ends. A control on the frame is selectively connectable to an internally generated source of electrical energy on the frame and an externally generated source of electrical energy located remotely from the frame. The control is connected to the lamps when the module is in the first position and the second position providing electrical energy to the lamps. A first mount is received by the proximal ends of the lamps and support the lamps in said housing. A second mount is received by the distal ends of the lamps and support the lamps in the housing.

It is an object of the present invention to provide a new method and apparatus for sterilizing sports fields.

A further object of the present invention is to provide a mobile ultraviolet sterilization vehicle that will maximize the sterilization of a sports field.

Yet a further object of the present invention is to provide an ultraviolet sterilization vehicle designed to have minimum impact on the environment.

An additional object of the present invention is to provide a method of minimizing infectious material on blades of a turf field wherein ultraviolet light is directed against the blades as the source of the ultraviolet light is moved in different directions across the field.

A further object of the present invention is to provide a new and improved mobile UV sterilization unit that can be used to sterilize objects located remotely from the unit.

Related objects and advantages of the present invention will be apparent from the following description.

DESCRIPTION OF THE PREFERRED EMBODIMENTS

Figure 1:
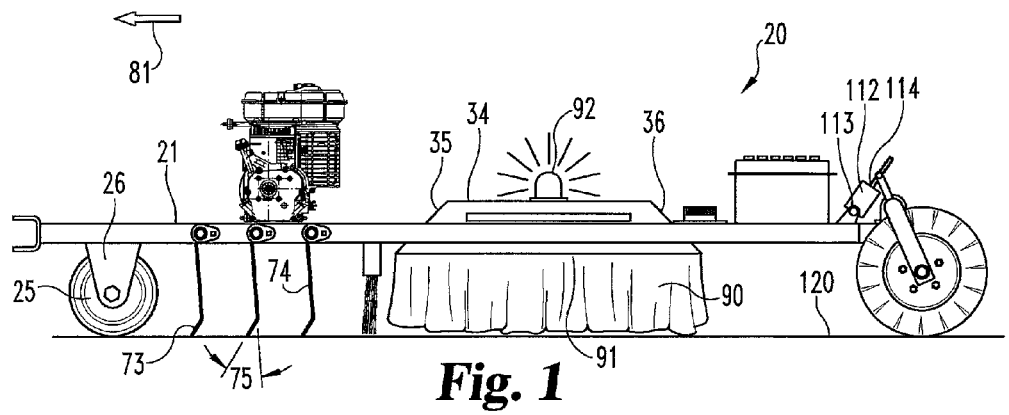
FIG. 1 is a side view of a second alternate embodiment of the mobile vehicle incorporating the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
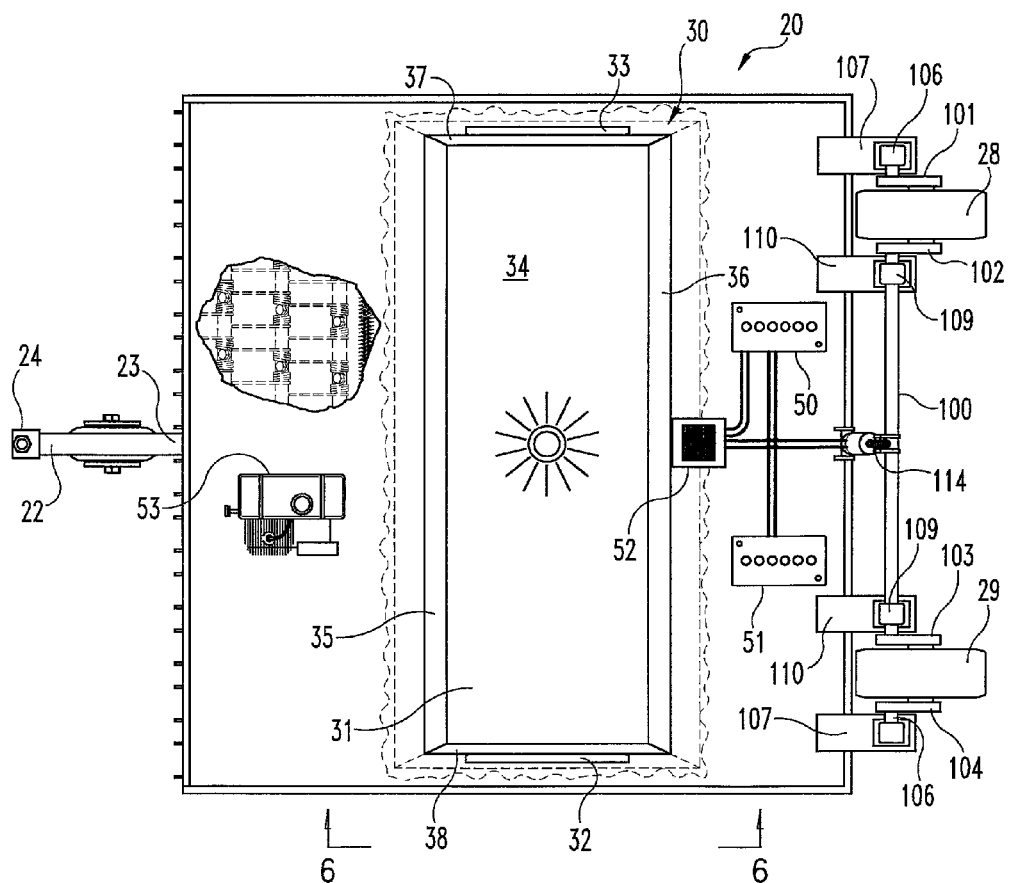
FIG. 2 is a fragmentary top view of the vehicle of FIG. 1.
Figure 3:
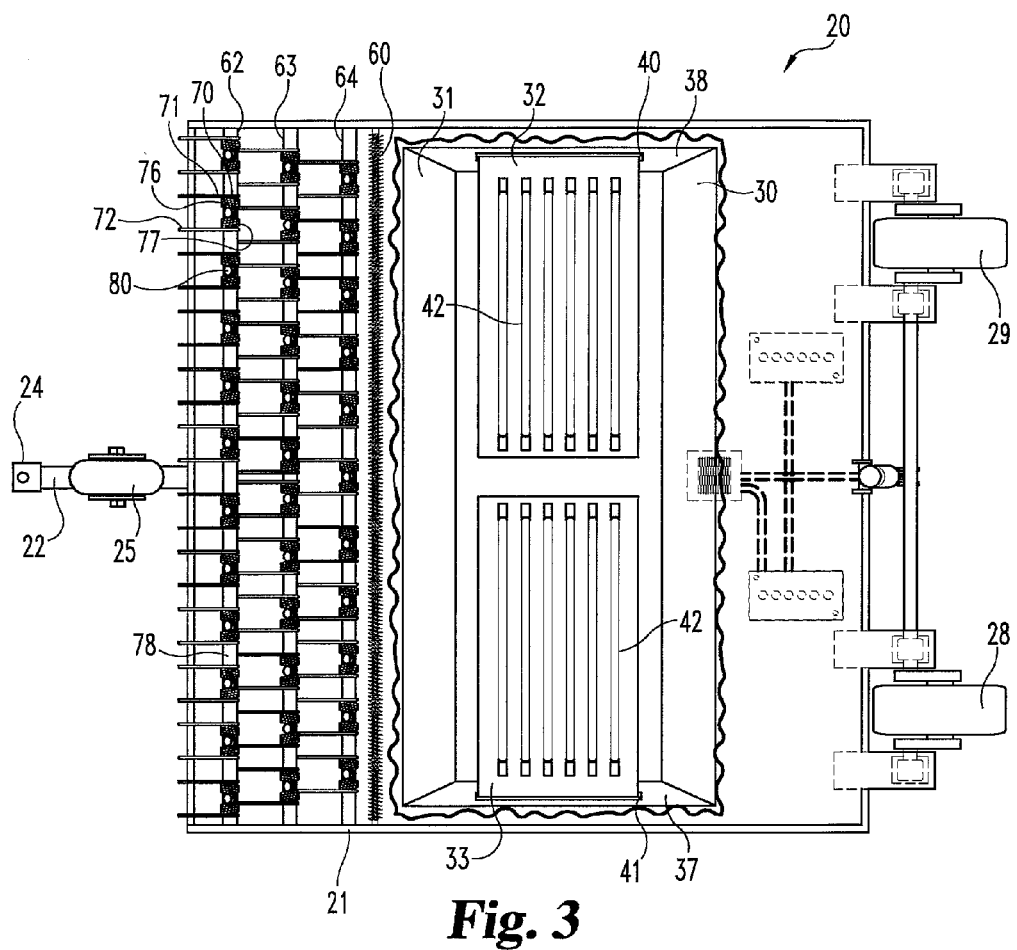
FIG. 3 is a bottom view of the vehicle of FIG. 1.

Referring now more particularly to FIGS. 1-3, there is shown the second alternate embodiment of a mobile vehicle 20 incorporating the present invention having a main frame 21 with a general rectangular configuration. A tow bar 22 has a proximal end 23 fixedly mounted to frame 21 and a distal end 24 forming a conventional hinge that can be coupled to a towing vehicle, such as a cart or tractor. Wheel 25 is rotatably mounted to a pair of flanges 26 fixedly mounted to bar 22 and depends therefrom allowing wheel 25 to engage the ground 120 and support frame 21. At the opposite end of the frame, a pair of wheels 28 and 29 is rotatably mounted to frame 21. Wheels 25, 28 and 29 support the vehicle as the vehicle is towed across a field.

A source of ultraviolet light 30 is mounted to frame 21 has a plurality of ultraviolet lamps to shine downwardly against the field. The source of ultraviolet 30 has a housing 31 closed on the top but opened on the bottom to allow the light from the ultraviolet lamps mounted therein to shine downwardly. Housing 31 has a top wall 34 joined to a pair of side walls 35 and 36 extending across the width of the vehicle and joined to a pair of end walls 37 and 38. Walls 35-38 extend angularly downward from the top wall and are fixed to frame 21.

A pair of identical ultraviolet lamp fixtures 32 and 33 is slidably mounted to housing 31 from the opposite sides thereof. End wall 38 has a slot 40 into which lamp fixture 32 is slidable. Likewise, end wall 37 is provided with a slot 41 through which lamp fixture 33 is slidable. Both lamp fixtures 32 and 33 rest atop shelves (not shown) provided within housing 31 to support the fixtures. Each lamp fixture 32 and 33 includes six removable ultraviolet lamps that are removably mounted thereto. The ultraviolet lamps 42 (FIG. 3) are arranged in rows extending lengthwise across the width of the vehicle. In the embodiment shown in FIG. 3, a total of 12 lamps are shown with six parallel lamps extending from one side of the vehicle to the approximate middle of the vehicle whereas the second set of parallel lamps 42 extend from the general middle location of the vehicle to the opposite side of the vehicle. Ultraviolet lamps are commercially available from a variety of lamp manufactures. Conventional male and mating female electrical connectors are provided in housing 31 to connect lamp fixtures 32 and 33 and thus lamps 42 to a source of electrical energy carried on the vehicle. The connectors are automatically electrically connected together by the action of fixtures 32 and 33 being slid into position.

A pair of identical 12 volt, 150 watt DC gel cell batteries 50 and 51 is mounted atop frame 21 and is connected via a conventional inverter 52 to lamps 42. The lamps operate on 115 volt AC with inverter 52 converting the DC power to AC power to energize the lamps.

A conventional generator or engine 53, is mounted atop frame 21 and is connected via inverter 52 to recharge batteries 50 and 51. In addition, inverter 52 may be connected by an auxiliary cord to a stationary source of alternating current, such as available in a building to recharge the batteries when not in use whereas engine 53 may be used to recharge the batteries both when the batteries are in use and not in use.

A brush 60 (FIG. 3) extends across the width of the vehicle and is attached and mounted to frame 21. Brush 60 includes a plurality of downwardly extending bristles to engage the synthetic field fibers to cause the fibers to extend generally vertical allowing the ultraviolet lamps to shine downwardly through the open bottom of housing 31 onto both sides of the synthetic fibers.

Three rows 62, 63 and 64 of downwardly extending tines are aligned to be parallel to each other and extend across the width of the vehicle and are mounted to frame 21. The tines are provided to contact the infill material between the synthetic upstanding fibers to move and turn over the infill material thereby exposing the material to the ultraviolet light. Brush 60 is positioned between the most rearward row 64 of tines and the source of ultraviolet light 30. The brush forms an engager that contacts the synthetic blades prior to the ultraviolet lamps shining thereon. The brush therefore positions the blades on the field to receive the ultraviolet light and destroy any infectious material thereon.

Figure 4:
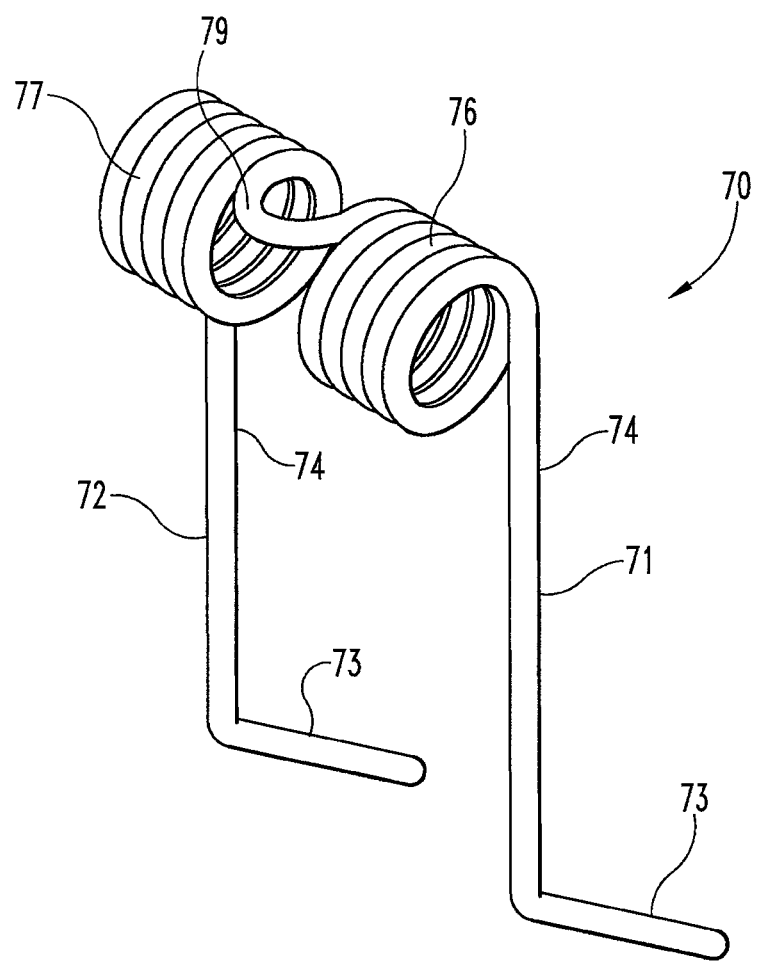
FIG. 4 is an enlarged perspective view of a pair of the tines for mounting to one of the rows of tines.
Figure 5:
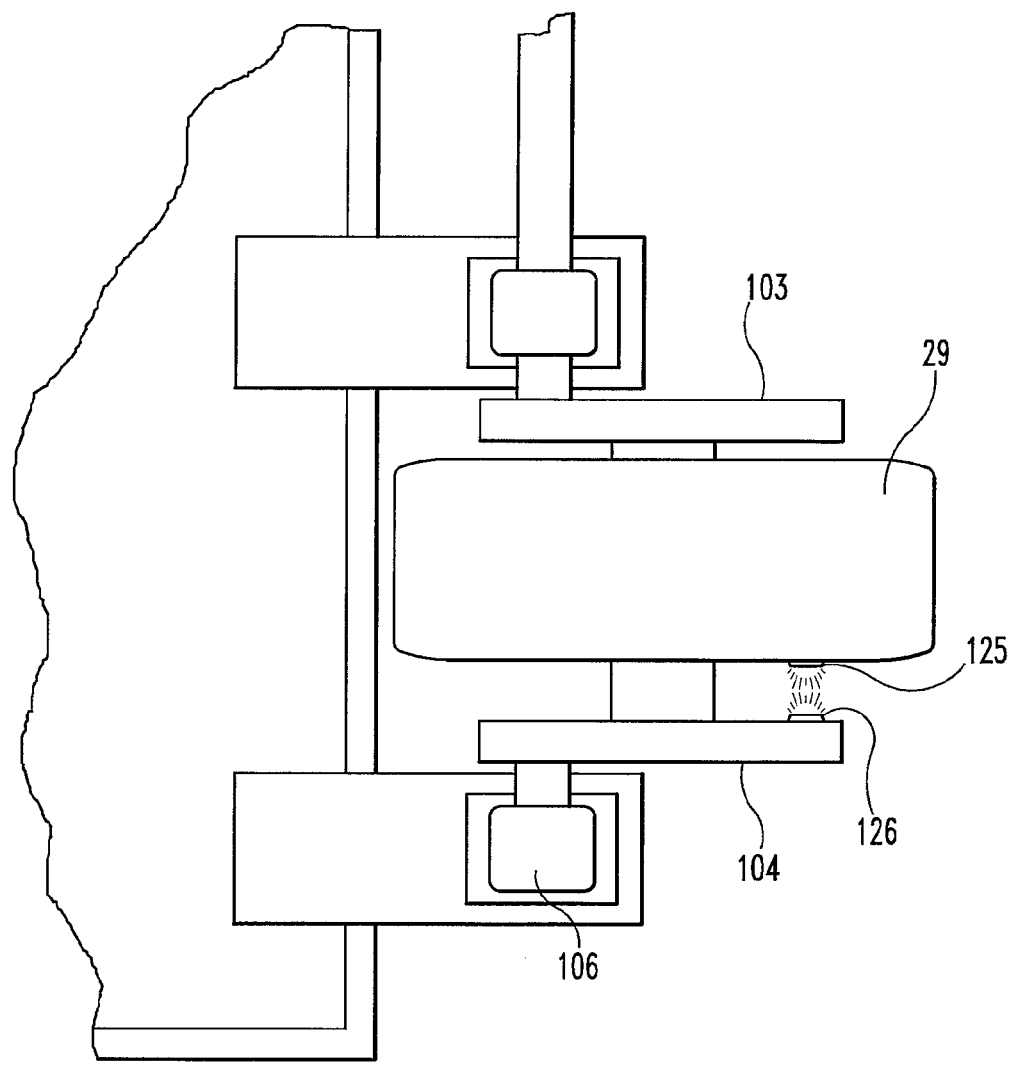
FIG. 5 is an enlarged fragmentary view of rear wheel 29 illustrating the positioning of the infrared sensor to detect stationary movements.
Figure 6:
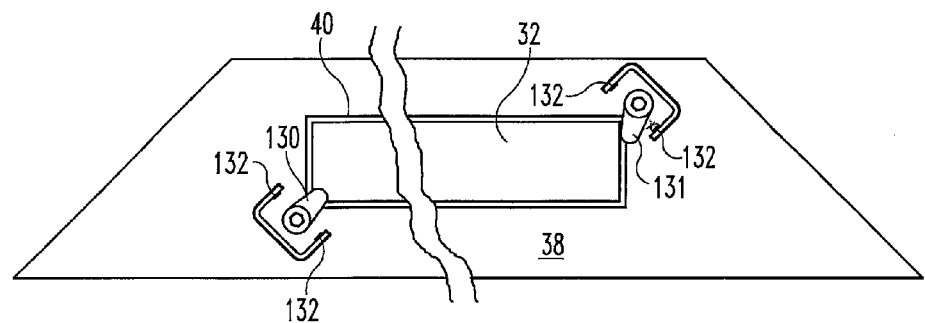
FIG. 6 is an enlarged fragmentary side view looking in the direction of arrows 6-6 of FIG. 2 of light fixture 32 held in place by a pair of cam locks.
Figure 7:
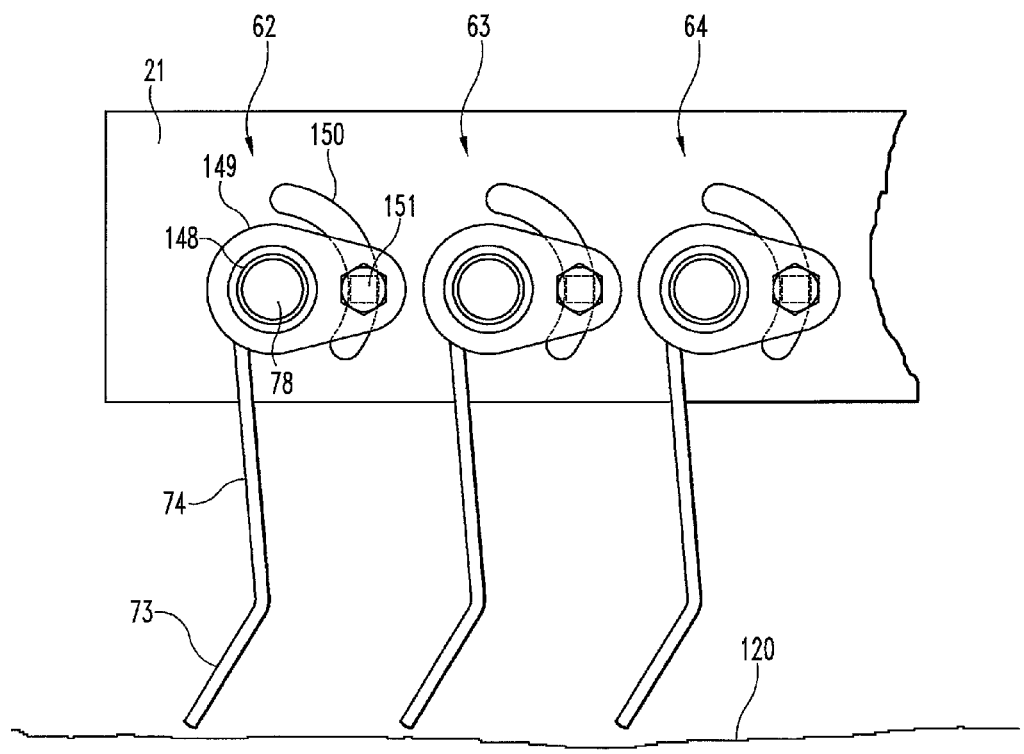
FIG. 7 is an enlarged fragmentary side view of frame 21 illustrating the mounting arrangement of the rows of tines.

Row 62 of tines will now be described it being understood that an identical description applies to tine rows 63 and 64. The tines are grouped in pairs. For example, pair 70 (FIGS. 3 and 4) includes a pair of wire shaped downwardly extending members 71 and 72 having bottom end portions 73 integrally joined to upwardly extending straight portions 74 with the proximal ends 73 (FIG. 1) arranged with respect to straight portions 74 at an approximate angle 75 of 40 degrees. The top end of straight portion 74 of tine 71 is integrally attached to a helically wound portion 76, in turn, integrally joined to a second helically wound portion 77, in turn, integrally joined to the top end of straight portion 74 of tine 72. Tines 71 and 72 are identical in construction.

Helical portions 76 and 77 are mounted to rod 78 (FIG. 1) that extends therethrough. Helical portion 76 and 79 are integrally joined together by a c-shaped middle section 79 (FIG. 4) that rests against a protruding head 80 (FIG. 1) extending outwardly from and fixedly mounted to rod 78. Head 80 extends into c-shaped section 79 thereby limiting movement of tines 71 and 72. As the vehicle moves in a forward direction 81 (FIG. 1), bottom ends 73 of each tine 71 and 72 contact the infill material between the upstanding synthetic fibers causing tines 71 and 72 to pivot backward towards the rear of the vehicle; however, c-shaped portion 79 in conjunction with the helical spring portion 76 and 77 return the tines to their original positions.

A flexible skirt 90 has a top end 91 mounted to frame 21 with the skirt extending down immediately above the field to prevent the ultraviolet light shining outward to an observer standing adjacent the vehicle. An LED light 92 is mounted to the top wall 34 of housing 31 to shine and provide a warning that the ultraviolet lamps are emitting ultraviolet light.

Wheels 28 and 29 are rotatably mounted to a pair of flanges, in turn, mounted to rod 100 that may be rotated to pivot the wheels up and down. For example, a pair of downwardly extending flanges 101 and 102 rotatably receive wheel 28 whereas downwardly extending flanges 103 and 104 rotatably receive wheel 29. The outward facing flanges 101 and 104 are mounted to bearings 106, in turn, fixedly mounted to flanges 107 affixed to frame 21. Rod 100 is rotatably received by bearings 109 mounted atop flanges 110 fixedly mounted to the frame. An actuator 112 (FIG. 1) has a bottom end 113 pivotally mounted to frame 21 and has an extendable rod 114 attached to rod 100 being operable to rotate rod 100. Rod 100 is located off center with respect to the rotational axis of wheels 28 and 29 with the result that rotation of rod 100 causes wheels 28 and 29 to pivot upwardly or downwardly with respect to the supporting surface 120 upon which the vehicle rides.

In operation, when moving the vehicle across supporting surface 120, when it is desired that the tines not contact the supporting surface, rod 114 is extended causing wheels 28 and 29 to pivot and move downwardly thereby lifting frame 21 to the point that the tines do not contact the supporting surface. In the event it is desired that the tines contact supporting surface 120, then rod 114 is retracted causing upward movement of wheels 28 and 29 thereby lowering frame 21 and allowing the bottom portions 73 of the tines to contact supporting surface 120.

The method of destroying the infectious material present on a field having synthetic upstanding blades using the vehicle shown in FIGS. 1-7 includes the step of moving a wheeled vehicle across the field while engaging the blades on the field by the vehicle. A source of ultraviolet light is carried on the vehicle and is positioned to shine the source of ultraviolet light downwardly against the blades to destroy the infectious material. The method includes the additional step of carrying a source of electrical energy on the vehicle to power the ultraviolet light. The engaging step includes the sub-step of brushing the blades to position the blades to receive the ultraviolet light thereby destroying the infectious material. Further, the method includes the additional step of shielding the ultraviolet light to provide safety for an operator of the vehicle by minimizing the visibility of the ultraviolet light from aside the vehicle. The method further includes the step of contacting the loose material between the blades by the vehicle as vehicle is moved across the field to expose the loose material to the ultraviolet light shining downwardly thereon. The step of contacting the loose material includes a sub-step of extending rigid members down from the vehicle and between the blades to move and turn over the loose material. In order to adjust the bottom ends of the tines relative to the field supporting surface, the method includes adjustably raising and lowering the vehicle by a pair of wheels located on the rear of the vehicle to controllably limit contact with the field. In the event the bottom ends of the tines are to be positioned apart form the supporting surface, then the rear wheels are moved downwardly sufficient so as to raise the vehicle frame and position the bottom ends of the tines apart from the supporting surface. On the other hand, if it is desired to control the amount of penetration of the tines into the loose material on the field, then the wheels are raised until the bottom ends of the tines penetrate the desired amount into the loose material. In order to maintain the ultraviolet lamps on the vehicle, the lamps are removably held to allow replacement thereof.

End walls 37 and 38 and side walls 35 and 36 of housing 31 as well as the top wall 34 of the housing provide inner surfaces to reflect the ultraviolet light downwardly. The slanted walls 35-38 are arranged at an angle to allow the ultraviolet light to extend beyond the immediate outline of each lamp.

In certain instances, it is desired to control the amount of ultraviolet light that shines upon the synthetic blades. That is, in the event the vehicle is stationary for a specified duration, then it is desirable to turn off the ultraviolet lamps to prevent the ultraviolet light from shining upon the synthetic blades for an unacceptable duration. To this extent, a commercially available infrared sensor 126 is mounted to flange 104 and is operable to detect movement of target 125 mounted to the mutually facing surface of wheel 29. A timing circuit is provided so that once rotation of wheel 29 stops for a predetermined time, for example 30 seconds, sensor 126 sends a signal to inverter 52 interrupting the flow of electrical energy to the ultraviolet lamps thereby turning the lamps off. As a result, the method disclosed herein includes deactivating the source of ultraviolet light when the vehicle is stationary on the field for a preset time.

In the event light fixtures 32 and 33 become accidentally dislodged from housing 31, micro switches are activated by cam locks normally holding the light fixtures in place to interrupt the flow of electrical energy to the light fixtures. For example, a pair of cam locks 130 and 131 is eccentrically mounted to end wall 38 and are designed to extend inwardly over the corners of light fixture 32. In the event the cam locks rotate allowing the light fixture 32 to move outwardly, then the cam locks contact conventional micro switches 132, in turn, connected to inverter 52 interrupting the flow of electrical energy to light fixtures and ultraviolet lamps. Cam locks identical to locks 130 and 131 along with switches identical to switches 133 are provided on wall 33 to hold fixture 33 and control the flow of electrical energy to fixture 33.

Some synthetic fields do not have crumb rubber (infill material) between the synthetic blade fibers. Thus, the main body of the supporting rod for each row of tines 62-64 may be rotated to rotate the tines upwardly apart from the field. For example, the ultraviolet lamp on the vehicle may be used to kill fungus on the blades of a standard golf green; however, it is imperative that the tines not extend down and engage the dirt between the non-synthetic blades of grass.

Each row of tines 62-64 (FIG. 3) includes a rod rotatably mounted at its opposite ends to the side walls of main frame 21 or interior walls, in turn, mounted to frame 21. Each rod includes a flange integrally secured thereto at each opposite end of the rod. The flange has a teardrop shape with the flange mounted eccentrically with respect to the rod. For example, rod 78 includes an end 148 (FIG. 7) integrally attached to one end of teardrop shape flange 149 positioned against the side wall of frame 21. The opposite end of flange 149 includes a slot 150 through which fastener 151 extends. Flange 149 can be pivoted about the longitudinal axis of rod 78 with fastener 151 moving between the opposite extremes of slot 150 to position the bottom ends 73 of the tines apart from supporting surface 120 or position the tips of bottom tine ends 73 into the supporting surface at a controlled distance.

Many variations are contemplated and included in the present invention. For example, the embodiment shown in the drawing has a single brush extending across the width of the vehicle between the tines and the UV lamps. It t is also possible to position a separate brush between rows 62 and 63 and another brush between rows 63 and 64 in order to increase the repositioning of the synthetic turf fibers and infill material therebetween.

Another variation of the present invention includes adding standard louvers to housing 31 in order to allow heat within the housing and generated by the UV lamps to escape upwardly. The UV lamps may take many different configurations. In the embodiment shown in the drawing, each lamp fixture 32 and 33 is approximately 36 inches wide by 36 inches in length and 6 inches in height. Each lamp fixture is shown as having six UV lamps removably mounted thereto; however, it is to be understood that at the present invention includes more than or less than two light fixtures and more than or less than six UV lamps for each lamp fixture.

Referring now more particularly to FIGS. 8-14, there is shown the first alternate embodiment of the mobile vehicle 200 having a main frame 201 with a general rectangular configuration. A tow bar 202 has a proximal end pivotally mounted by hinge 203 (FIG. 9) about a horizontal axis to main frame 201 to enable the tow bar distal end 204 to move up and down and sideways for attachment to the towing vehicle. A pair of conventional front wheels 205 (FIG. 10) are each rotatably mounted by conventional brackets about a horizontal axis with the brackets then being pivotable about a vertical axis allowing the wheels to rotate and swivel in a conventional manner as the frame is towed across a field. A pair of rear wheels 206 are rotatably mounted each about a horizontal axis by brackets fixedly attached to main frame 201 to enable the rear wheel to rotate as the main frame is towed. The rear wheels do not swivel. Likewise, frame 201 is not moved vertically with respect to the front wheels or rear wheels since the actuator 112 (FIG. 1) provided in the second embodiment of the mobile vehicle is not included in the first embodiment of the mobile vehicle 200 shown in FIG. 8.

A source of electrical energy or generator 207 (FIG. 8) is mounted atop main frame 201 by conventional brackets and is normally enclosed by housing 208 having an edge portion 209 hingedly secured to main frame 201. Housing 208 is shown in the upward position thereby revealing source 207; however, it is to be understood that in normal operation housing 208 is pivoted downward to conceal the source of electrical energy 207. A plurality of louvers are provided in the side walls of housing 208 to enable air to circulate around the source of electrical energy.

A plurality of ultraviolet lamps are removably mounted to frame 201 and operate on 115 volt AC. The source of electrical energy 207 includes a gasoline operated internal combustion engine 210 having a gasoline storage tank 211 provided in a combination unit, such as available from Honda under Model Nos. EU1000i or EU2000i. The electrical output of the internal combustion engine is 12 volts DC used to power status light bulbs located on the main frame and also capable to recharge batteries 213. An inverter 212 is mounted to the main frame and is operable to convert 12 volts DC from the engine to 115 volts AC supplied to the ultraviolet lamps. In the event it is desired to operate the mobile sterilization unit in a quieter mode, the batteries 213, preferably gell cell batteries, are provided which, in turn, are electrically connected to inverter 212 for purposes of converting the battery direct current output to 115 volt AC supplied to the ultraviolet lamps. In order to recharge batteries 213, engine 209 may be activated thereby connecting the direct current output of the engine to batteries 213 for the recharging thereof. Alternatively, the batteries may be recharged by an external source other than the engine.

In order to control the spacing of the ultraviolet lamps with respect to the turf field, the lamps are removably mounted in a lamp housing 220 (FIG. 8) which is movable vertically by operation of mechanism 221. The mechanism 221 includes a pair of upstanding brackets 222 (FIG. 8a) having bottom ends fixedly mounted to frame 201 with the top ends of members 222 having an internally threaded bar 223 through which worm drive or gear 224 threadedly extends. The outer end 225 of the worm gear is attached to a hand crank 226 whereas the opposite end of worm gear 224 is connected to a pair of spaced apart members 227 extending rearwardly. The forward ends of members 227 are connected together by plate 228 in which the rearward most end of worm gear 224 is held captive. Thus, rotation of worm gear 224 results in members 227 moving forward or rearward along a horizontal axis as the crank 226 is rotated.

Rod 230 (FIG. 8) has opposite ends 231 and 232 rotatably mounted by brackets 233, in turn, rotatably attached to frame 201. A pair of upstanding arms 234 have bottom ends fixedly mounted to rod 230 and top ends connected together by fastener 235 extending through a slot in the rearward ends of members 227. Thus, rotation of the crank 226 in a first direction causes members 227 to move rearwardly which causes arms 234 to pivot in a counterclockwise direction as viewed in FIG. 8 thereby rotating rod 230.

A second rod 240 has opposite ends 241 rotatably mounted in downwardly extending brackets 242 supporting the rod 240 and allowing the rod to rotate about a horizontally extending axis. A second pair of arms 244 have bottom ends fixedly attached to rod 240 and top ends secured by fastener 245 to the rearward end of connecting members 246. The forward end of members 246 are attached by fastener 235 to arms 234. As a result, rotation of worm gear 224 causes coordinated movement of arms 234 and 244 and thus coordinated rotation of rods 230 and 240. When the crank is rotated to move members 227 rearwardly, arms 234 and 244 are caused to rotate along with rods 230 and 240 in a counterclockwise direction as viewed in FIG. 8.

A forward pair of downwardly extending slotted brackets 250 have top ends fixedly attached to frame 201 with the two brackets 250 located on the opposite sides of frame 201. Likewise, a rearward pair of slotted brackets 251 have top ends fixedly attached to frame 201 with the two brackets 251 located on the opposite sides of frame 201. A front pair of links 252 have forward ends connected to the opposite ends of rod 230 and move therewith. Likewise, a pair of rearward links 254 are connected to the opposite ends of rod 240 and move therewith. Links 252 are located on the opposite sides of frame 201. Likewise, links 254 are located on the opposite sides of frame 201. The most rearward ends 255 of links 252 extend through the vertical slot of brackets 250 and are connected to lamp housing 220. Likewise, the rearward ends 256 of the pair of links 254 extend through the vertical slot of brackets 251 and are attached to the rearward portion of the lamp housing. Rotation of crank arm 226 in a first direction causes worm gear 224 to rotate thereby resulting in rearward movement of members 227 and 246 with the resultant counterclockwise movement of rods 230 and 240, in turn, causing the forward pair of links 252 and the pair of rearward links 254 to pivot with the opposite ends of rods 230 and 240. The rearward ends 255 and 256 of links 252 and links 254 thereby move downwardly in the slots of brackets 250 and 251 spacing lamp housing 220 and the ultraviolet lamps mounted therein apart from the turf field a first distance. The slots may be designed so that when the rearward ends of links 252 and 254 are located at the bottom of the slots, the ultraviolet lamps are spaced apart the optimum distance from the field to achieve maximum sterilization results. Excellent results have been obtained by positioning the lamps two inches above the sports field. Rotation of the crank handle in a second direction opposite of the first direction causes worm gear 224 to rotate thereby moving members 227 and 246 forwardly resulting in clockwise motion as viewed in FIG. 8 of rods 230 and 240. As a result, the rearward ends 255 and 256 of links 252 and 254 move upwardly in the slots of brackets 250 and 251 raising the lamp housing and ultraviolet lamps contained therein from the turf field a distance greater than the optimum distance to enable transportation of the mobile vehicle when the ultraviolet lamps are not activated.

When the mobile unit is being used to sterilize the turf field, the lamp housing and ultraviolet lamps are in the lower position. A plurality of rollers 260 (FIG. 8) are rotatably mounted to the lamp housing to protect the ultraviolet lamps when in the lower sterilization position. The rollers are rotatably mounted and extend slightly beneath the lamp housing bottom edge and automatically cause the lamp housing to move upward in the event the rollers encounter a foreign object such as a rock. The rollers do not normally contact the ground or field unless a sudden rise the ground or field is encountered. In the embodiment shown in FIG. 10, three such rollers are mounted to the lamp housing on the front portion of the lamp housing and three rollers are rotatably mounted to the rear portion of the lamp housing.

Lamp housing 220 (FIG. 8) is a four sided rectangular frame having an open top and an open bottom. The housing includes a pair of side walls 271 and 272 (FIG. 10) joined to end walls 273 and 274. A ledge 276 (FIG. 12) is integrally attached to rear wall 274 and extends between side walls 271 and 272. A second inwardly extending ledge 277 is attached to front wall 273 and extends between the side walls 271 and 272. Two lamp modules 290 and 291 (FIG. 8) are inserted into housing 220 from atop of the lamp housing and rest therein on ledges 276 and 277.

Figure 14:
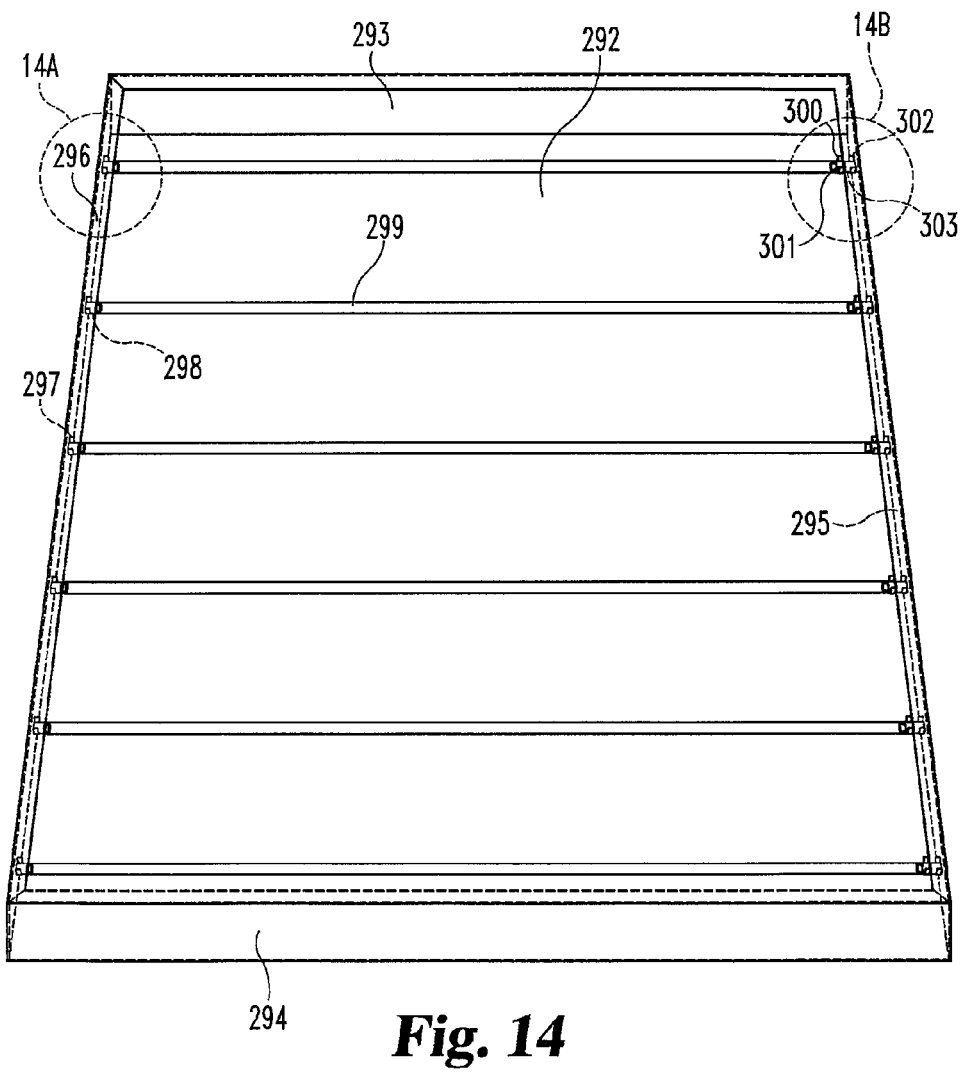
FIG. 14 is an enlarged bottom perspective view of a lamp module with ultraviolet lamps mounted therein.
Figure 14A:
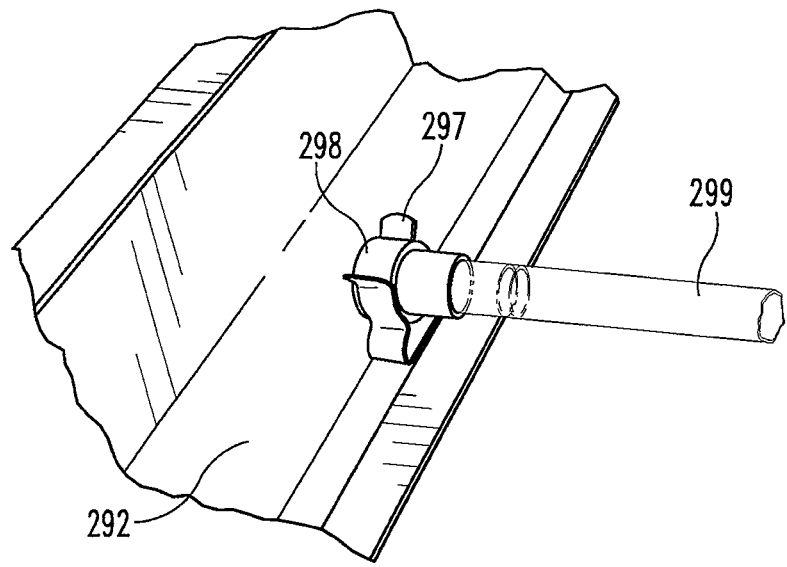
FIG. 14a is an enlarged fragmentary view of the distal end of a ultraviolet lamp held by a clip shown in the enclosed circle 14a of FIG. 14.
Figure 14B:
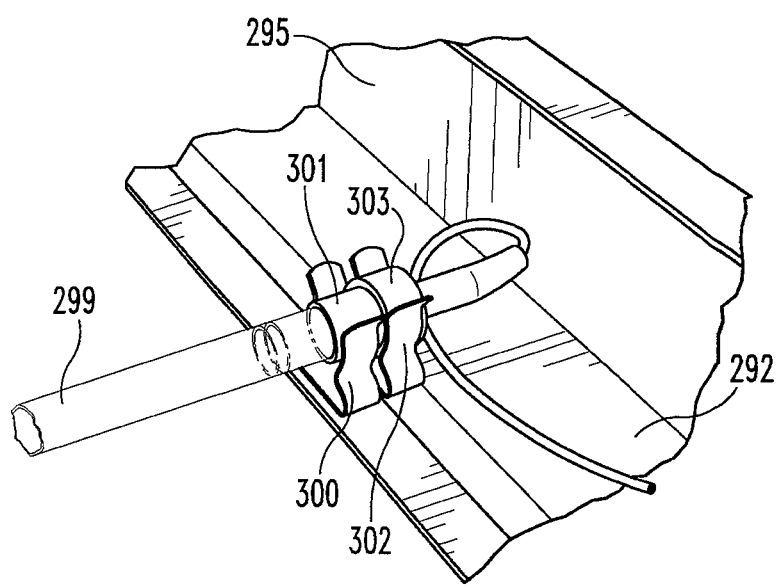
FIG. 14b is an enlarged fragmentary view of the proximal end of a ultraviolet lamp held by a clip along with the attached electrical connector shown in the enclosed circle 14b of FIG. 14.

Lamp module 290 (FIGS. 13 and 14) will now be described it being understood that an identical description applies to lamp module 291. Lamp module 290 is five sided container having a closed top wall 292 joined to a pair of end walls 293 and 294 and a pair of side walls 295 and 296. Four handles 297 are attached to top wall 292 and project thereabove. The bottom of lamp module is open to allow the ultraviolet lamps contained therein to shine downwardly. In the version of the lamp module depicted in FIG. 13, a total of six ultraviolet lamps are removably mounted therein and are arranged in parallel rows extending in a direction across the width of frame 201. The inside surface that faces downwardly of top wall 292 (FIG. 14) is highly reflective in order to reflect downward energy from the ultraviolet lamps towards the turf field. Fixedly mounted to top wall 292 and facing downwardly are six clips 297 having spring biased arms to releasably hold ends 298 of lamps 299. Six additional clips 300 identical to clips 297 are mounted to wall 292 to releasably hold the opposite ends 301 of the ultraviolet lamps. A third set of clips 302 identical to clips 297 are mounted to top wall 292 immediately adjacent to wall 295 to hold a plurality of commercially available electrical connectors 303. Clips 302 which hold the connectors 303 cooperatively support with clips 300 the proximal ends 301 of the lamps. Connectors 303 may have female sockets into which the outwardly projecting pins of lamp ends 301 project. Likewise, ends 301 of the ultraviolet lamps may have inwardly projecting sockets to electrically receive outwardly projecting pins of electrical connectors 303. All six of the connectors 303 are then connected by conventional wiring to the source of electrical energy. FIGS. 14a and 14b illustrate clips 297, 300 and 302 holding lamp 299 and connector 303.

Figure 12:
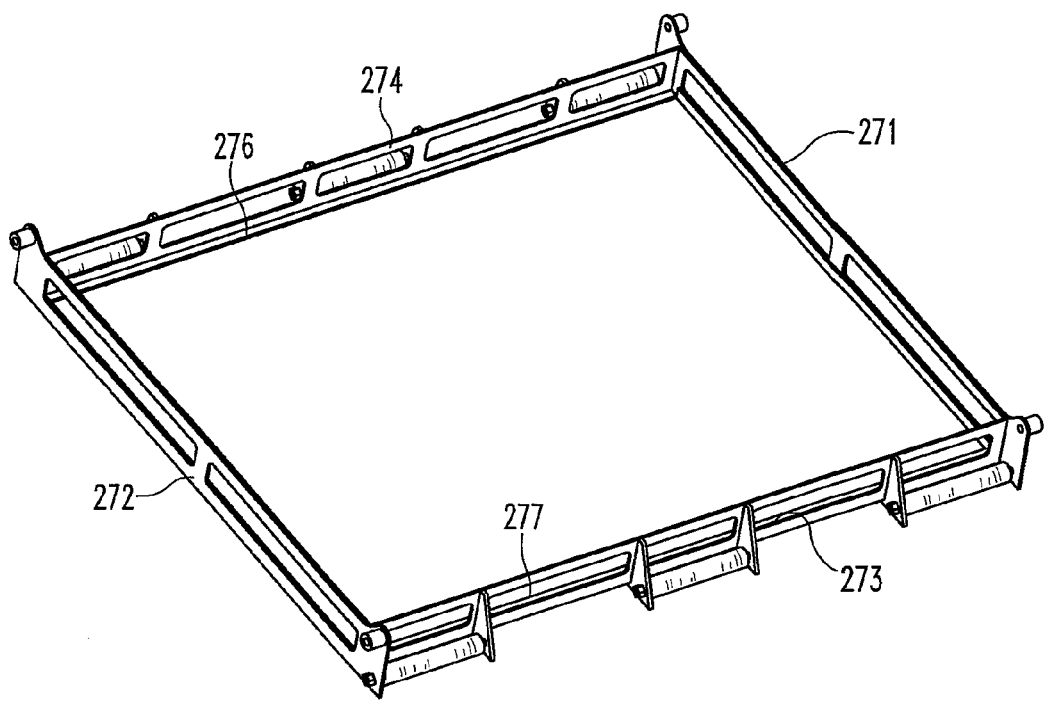
FIG. 12 is an enlarged top perspective view of the lamp housing.
Figure 13:
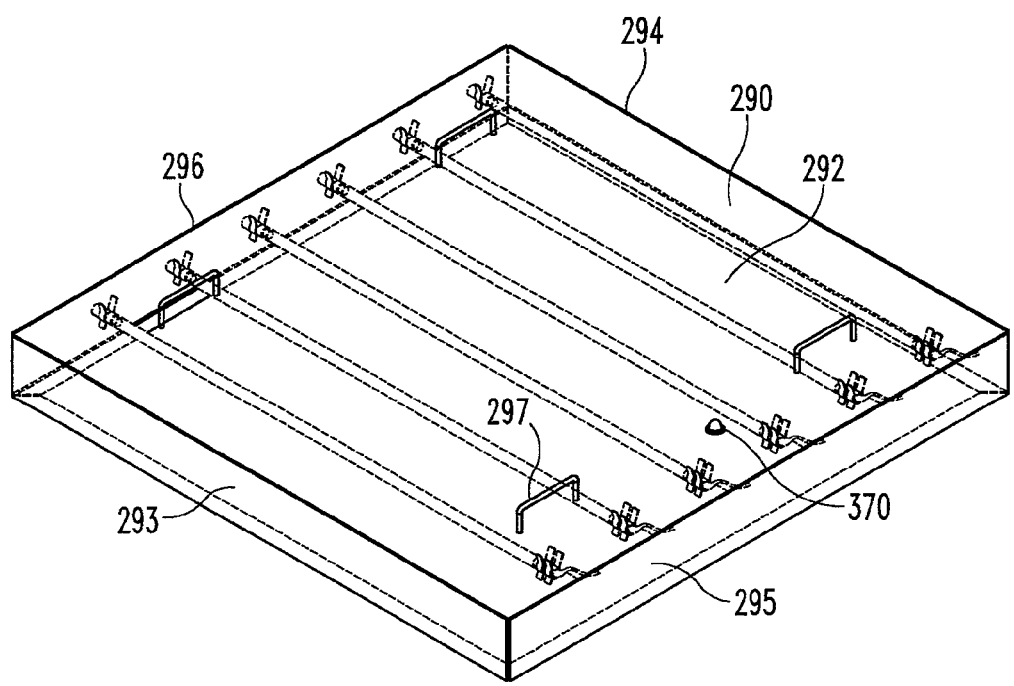
FIG. 13 is an enlarged top perspective view of a lamp module.

In order to install or remove lamp modules 290 and 291, the lamp housing 220 is lowered to its lowest position by cranking handle 226 and then slipping the lamp modules over and into the lamp housing 220 from the sides of frame 201. Depending upon the spacing, links 254 may be disassembled in order to slip each lamp module through the gap between frame 201 and lamp housing 220 until each lamp module is immediately over the lamp housing and then dropping into place resting atop ledges 276 and 277 (FIG. 12). Thus, lamp module 290 may be inserted from the right as viewed in FIG. 8 through gap 306 between frame 201 and the lamp housing whereas the second lamp module 291 is inserted through a similar gap on the opposite side of the frame. Handles 297 are provided to facilitate holding the lamp module as is inserted or removed from the lamp housing.

Vehicle 200 includes the downwardly extending brushes 60 (FIG. 10) previously described for vehicle 20 (FIG. 3). Further, the rows 62, 63 and 64 of tines extend downwardly from vehicle 200 (FIG. 10) previously described for vehicle 20 (FIG. 3). The locations and functions of the brushes and tines are the same for vehicle 200 as described for vehicle 20. Since vehicle 200 does not include actuator 112 which raises the frame of vehicle 20 thereby also raising the brushes and tines for transportation during the non-sterilization condition, the brushes and tines of vehicle 200 may be mounted on a secondary frame pivotally mounted to frame 201 of vehicle 200. The secondary frame maybe pivoted upwardly thereby disengaging the brushes and tines when it is desired to move vehicle 200 without the brushes and tines engaging the turf field. The secondary frame may be releasably locked in the upward, non-use position by means of a removably pin extendable into frame 201 and the secondary frame. Certain fields do not include loose material between the blades and thus, the blades and tines may be stored in the upward position.

Figure 8:
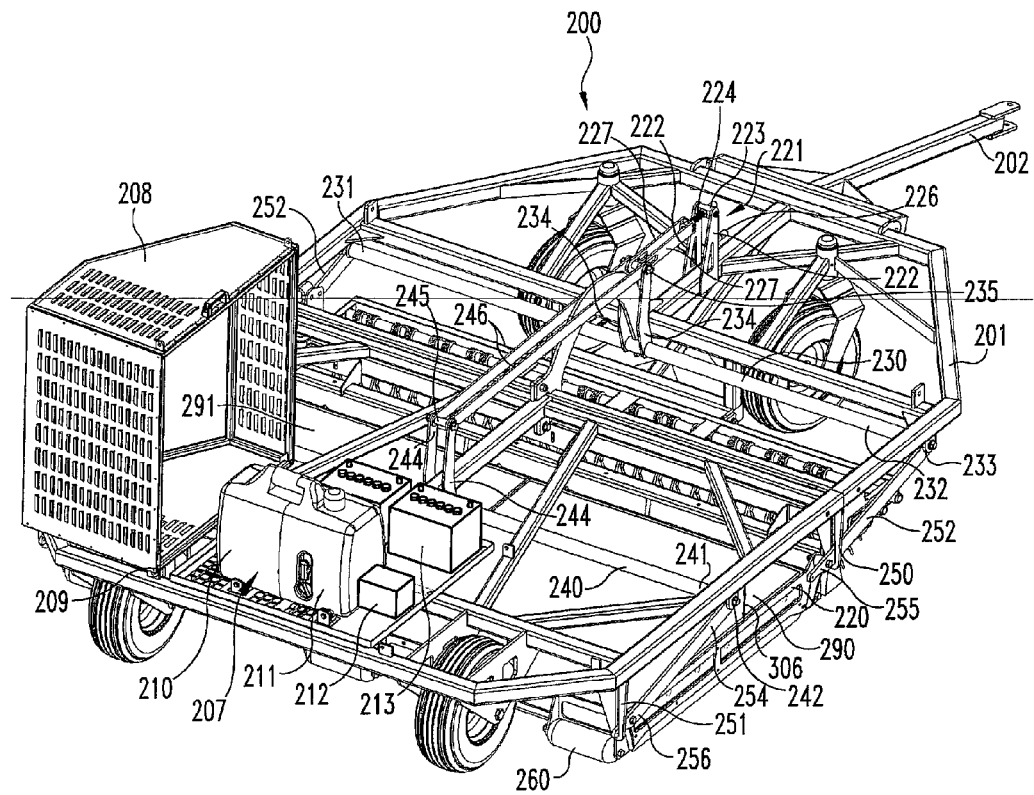
FIG. 8 is a rear perspective view of the first alternate embodiment of the vehicle incorporating the present invention.
Figure 8A:
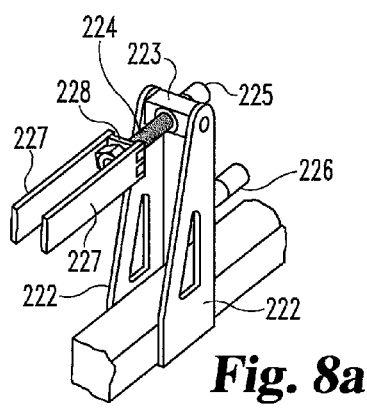
FIG. 8a is a fragmentary rear perspective view of the crank mechanism.
Figure 9:
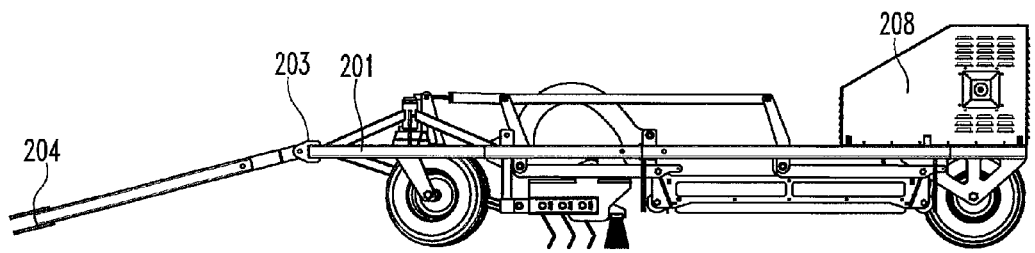
FIG. 9 is a left side view of the vehicle of FIG. 8.
Figure 10:
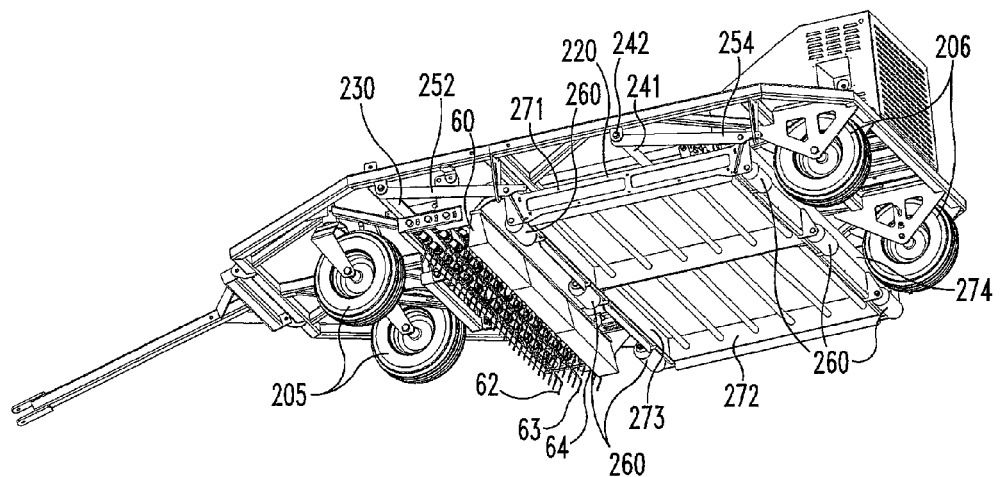
FIG. 10 is a bottom perspective view of the vehicle of FIG. 9.
Figure 11:
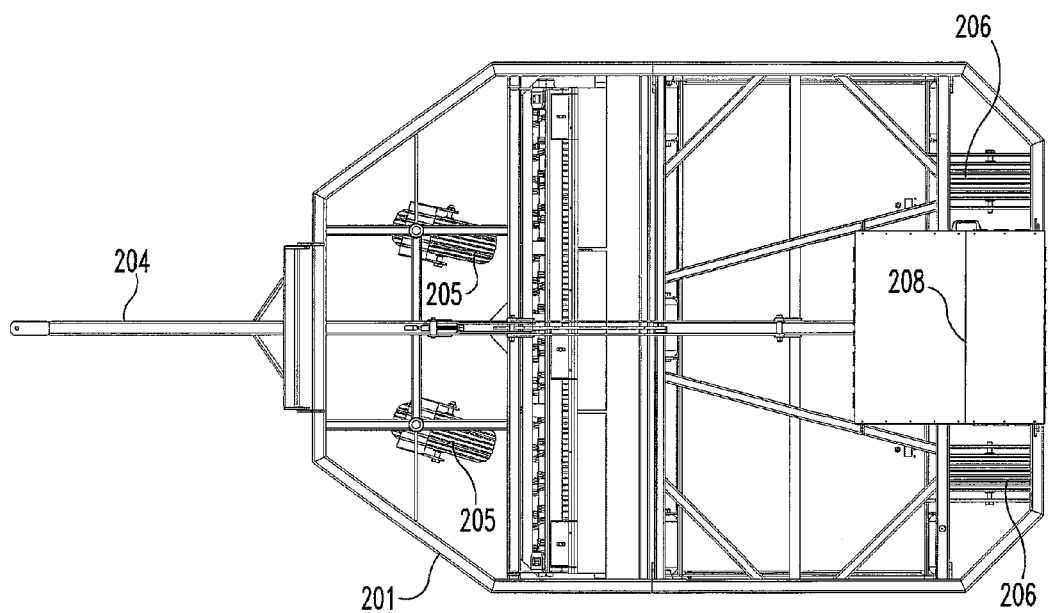
FIG. 11 is a top view of the vehicle of FIG. 8.

Skirt 90 described for vehicle 20 and illustrated in FIG. 1 is also provided for vehicle 200 but has been deleted from FIG. 8 in order to more fully illustrate the structure of the vehicle. Such a skirt is attached to frame 201 and extends downwardly around the light housing 220 to limit a person from seeing the ultraviolet light shinning down from the ultraviolet lamps.

Figure 15:
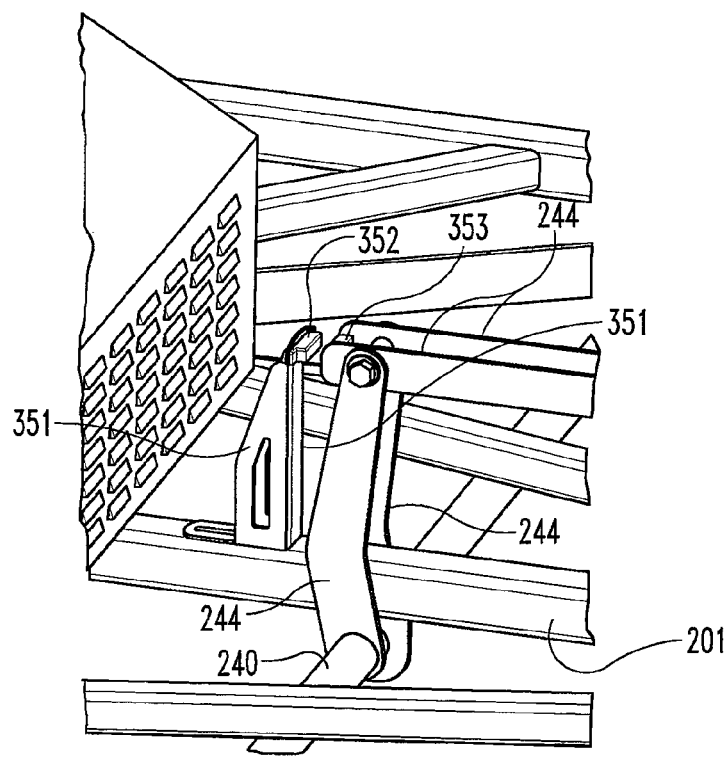
FIG. 15 is a fragmentary view of the vehicle illustrating a safety switch for allowing flow of electrical energy to the ultraviolet lamps only if the light housing is in the downward position.

A safety switch (FIG. 15) is mounted to frame 201 to prevent the flow of electrical energy to the ultraviolet lamps unless the light housing 220 is positioned at the most bottom position spacing the ultraviolet lamps the required distance to sterilize the field. The switch includes a pair of arms 351 having bottom ends slidably mounted to frame 201 and top ends with a bumper 352 mounted thereto and aligned with a corresponding bumper 353 mounted to the top ends of arms 244. When the light housing 220 is in the upward position, bumpers 352 and 353 are spaced apart positioning the forwardly spring biased switch 350 in the forward position illustrated in FIG. 15. As arms 244 move rearwardly pivoting rod 240 counterclockwise as viewed in FIG. 15, links 254 pivot counterclockwise as viewed in FIG. 8 forcing the light housing to the bottom position while bumper 353 contacts bumper 352 moving arms 351 rearwardly and closing the switch allowing electrical energy to flow from the source of electrical energy to the ultraviolet lamps.

Figure 16:
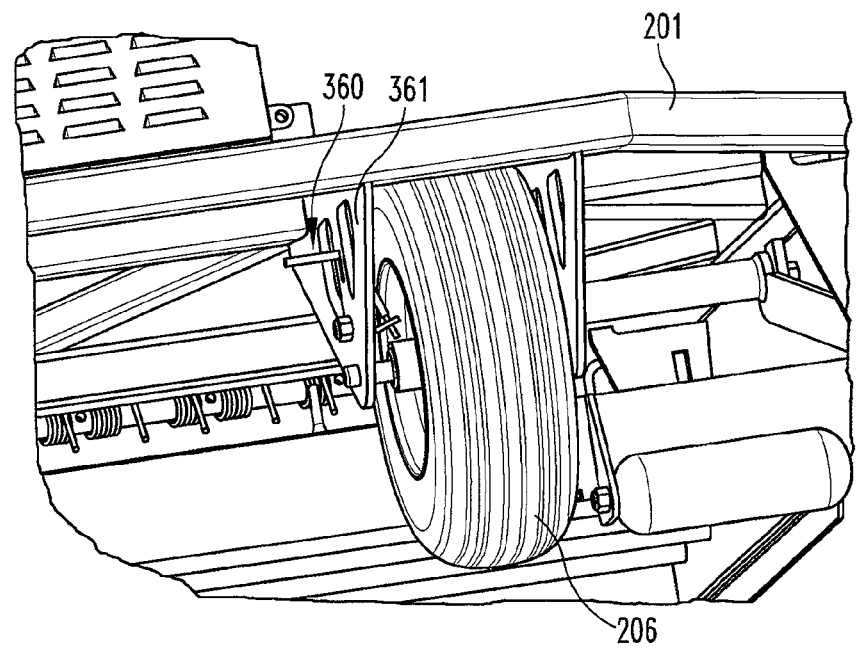
FIG. 16 is a fragmentary rear view of the vehicle illustrating a motion sensor for detecting motion of a rear wheel.
Figure 17:
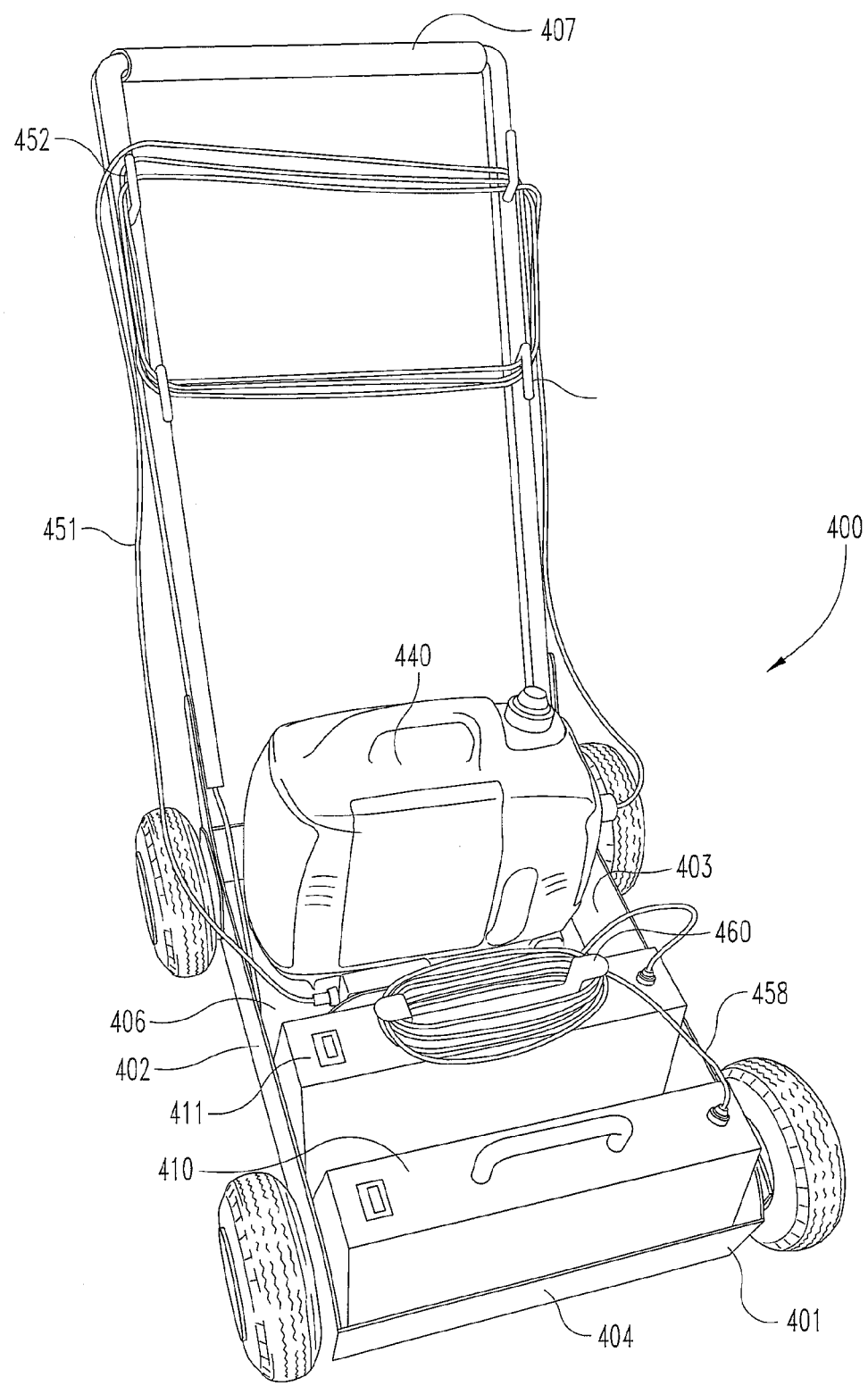
FIG. 17 is a top perspective view of the preferred embodiment of the mobile UV sterilization unit.
Figure 18:
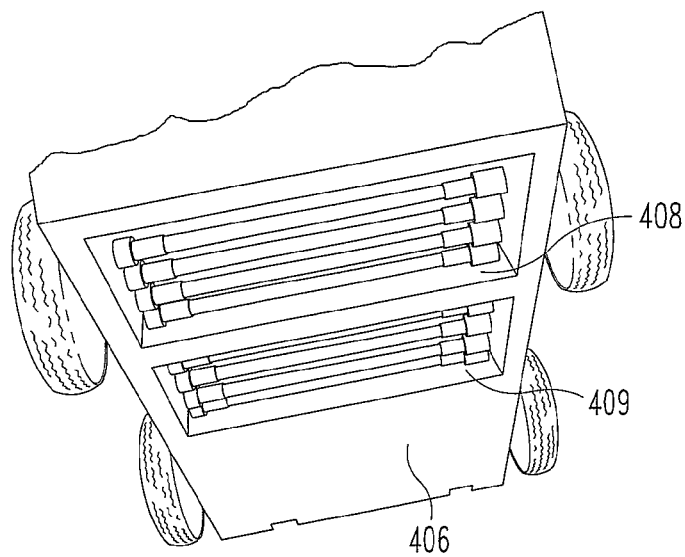
FIG. 18 is a bottom fragmentary perspective view of the unit of FIG. 17.

A second safety switch 360 (FIG. 16) is mounted to wheel mounting bracket 361. Switch 360 is a standard commercially available motion sensor and monitors motion of wheel 206. The switch is operable to interrupt the flow of electrical energy from the source of electrical energy to the ultraviolet lamps in the event the wheels have not moved for more than a specified time, for example fifteen or thirty seconds. Switch 360 prevents the turf from degradation in the event the vehicle is stationary for a more than a specified time with the lamps in the on position. A kill switch, not shown, is in series with the wiring from the source of electrical energy to the lamps to allow immediate interruption of the flow of electrical energy to the lamps when depressed for use in an emergency. Likewise, a reset switch is provided to reactivate the flow.

Each lamp module 290 and 291 include an indicator light 370 (FIG. 13) connected in series with the wiring to the lamp connectors to indicate when the lamps are activated in the on position.

The method of minimizing the infectious material of the blades of a synthetic or living turf field includes providing vehicle 200 with the downwardly shining ultraviolet lamps and spacing the lamps apart from the fields a first distance. Excellent results have been obtained by spacing the lamps apart from the field a distance of 2 inches to 3 inches. In such a case, the vehicle was moved across the field at an approximate speed of 8 to 10 miles per hour. Best results have been achieved by moving the vehicle across the field in a first direction, for example, across the width (side to side) of the field and also across the field in a second direction different from the first direction, for example, across the length (end to end) of the field and also across the field in a third direction different from both the first direction and second direction, for example, diagonally (corner to corner) across the field while the lamps shine ultraviolet energy against the blades of the turf field. By moving the vehicle across the width, length and diagonal of the field, the lamps shine ultraviolet energy against different portions of the blades of the field increasing the exposure of the infectious material to the ultraviolet energy. In addition, the method includes the step of extending downwardly an engager, such as the brush and tines disclosed herein, which contact the blades and the loose material between the blades of the field thereby repositioning the blades and loose material to receive the ultraviolet light as the vehicle is moved in different direction across the field.

The ultraviolet lamps used with the vehicle and method described herein are commercially available. For example, such lamps are manufactured by American Ultraviolet Company, Lebanon, Ind. under Model Number GTL 36 GG. The lamps may be Teflon coated to provided extra safety in the event the lamp breaks. Excellent results have been obtained with forty watt lamps. The ballast units used with the ultraviolet lamps may be mounted within the lamp modules.

Figure 19:
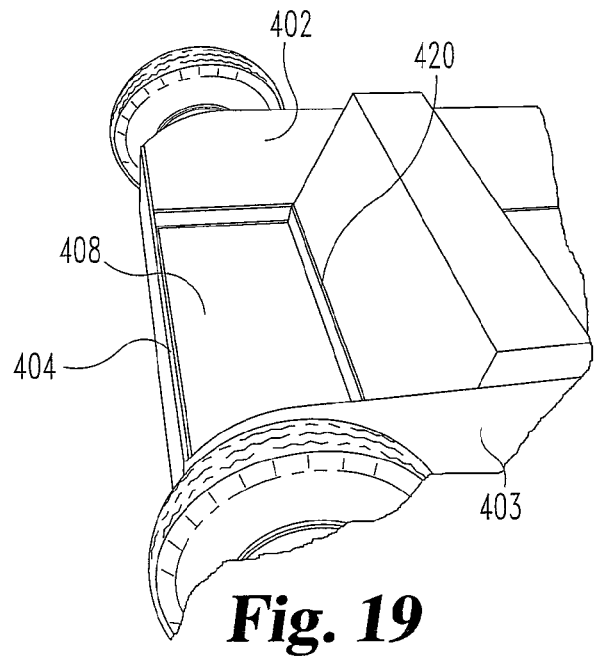
FIG. 19 is a top fragmentary perspective view of the front end of the unit of FIG. 17 with one lamp module removed therefrom.
Figure 20:
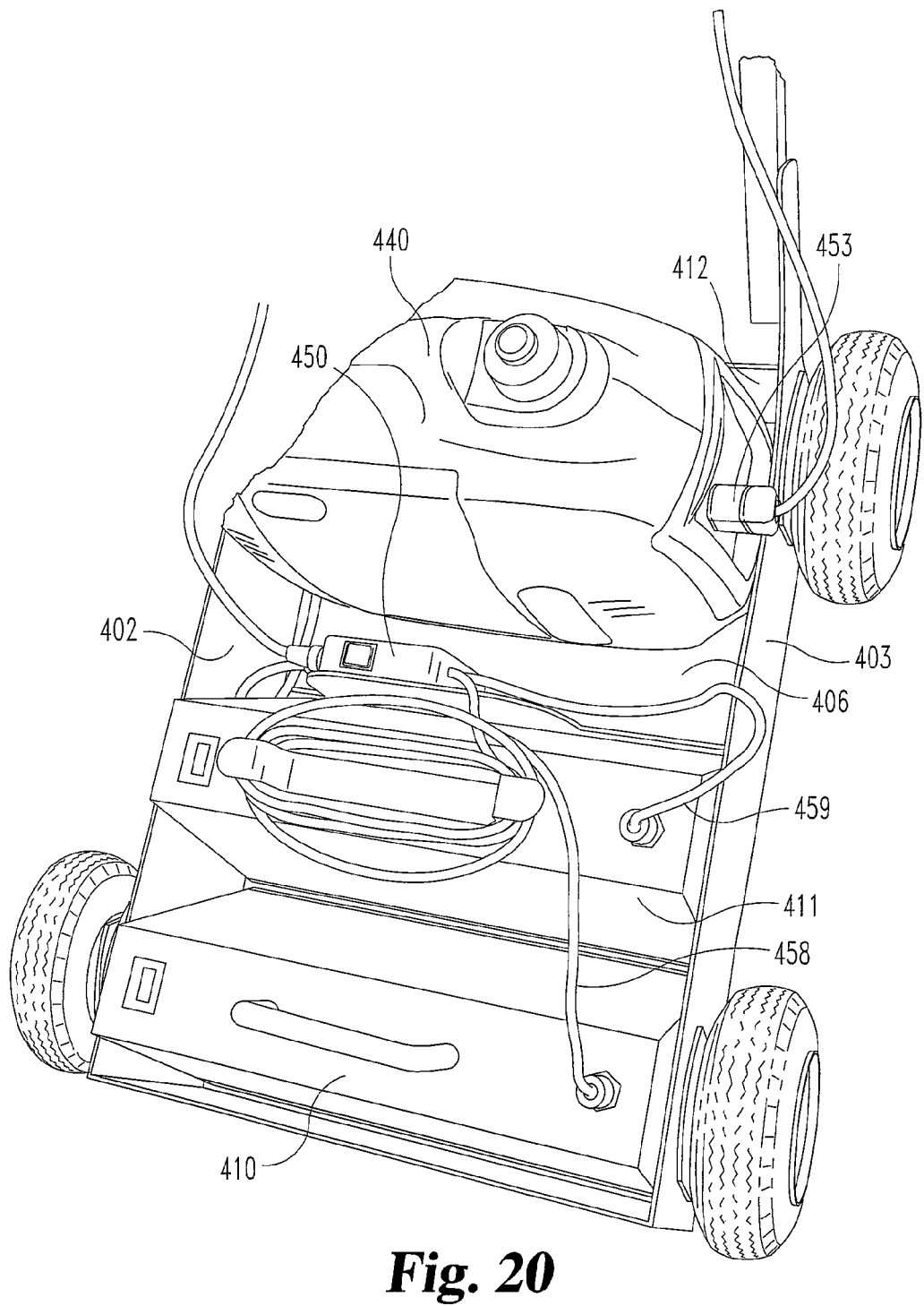
FIG. 20 a fragmentary top view of the unit of FIG. 17.
Figure 21:
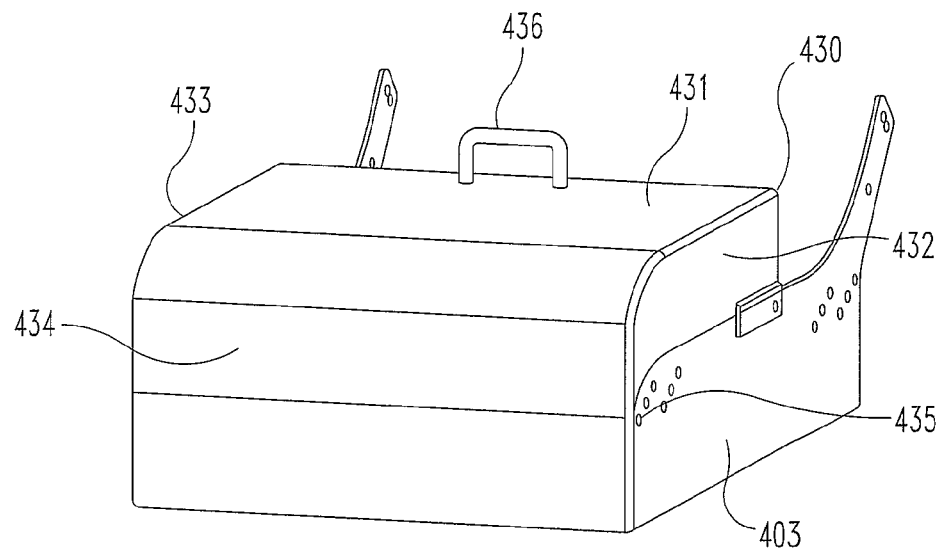
FIG. 21 is a fragmentary perspective front view of the cover removably enclosing the first lamp module and second lamp module.

The preferred embodiment of the mobile UV sterilization unit 400 is shown in FIGS. 17-24. Unit 400 includes a wheeled carriage 401 consisting of a main frame with a pair of side walls 402 and 403 joined to a front end wall 404 and a rear end wall 412 (FIG. 20) forming a box like construction having a bottom wall 406 joined to the side walls and end walls (FIG. 20). A pair of front wheels and rear wheels are rotatably mounted to side walls 402 and 403 to support a pair of lamp modules and a generator. A handle 407 extends rearwardly thereby allowing a person to apply pushing force to the handle and propel the carriage across a field to be sterilized.

The bottom wall 406 (FIG. 18) has two rectangular openings 408 and 409 aligned with two ultraviolet lamp modules 410 and 411 (FIG. 17) to allow the ultraviolet light from the ultraviolet lamps mounted within the modules to shine downwardly against the field to be sterilized as the unit is pushed across the field.

Ultraviolet lamp module 410 (FIG. 20) will now be described it being understood that an identical description applies to ultraviolet lamp module 411. Lamp module 410 (FIG. 23) consists of a five sided box or container including a top wall 413 joined to end walls 414 and 415 that are also joined to a pair of side walls 416 and 417. Side walls 416 and 417 diverge as they extend downwardly from the top wall 413. A handle 418 is mounted to the top wall 413 to allow the lamp module 410 to be grasped and pulled upwardly from between the carriage side walls 402 and 403 and front end wall 404 and intermediate wall 420 (FIG. 19).

Figure 24:
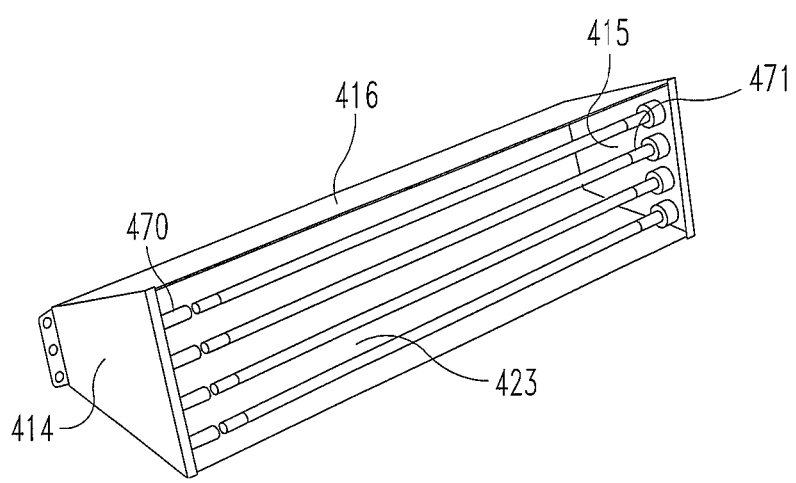
FIG. 24 is a bottom perspective view of the lamp module of FIG. 23.

Lamp module end walls 414 and 415 are spaced apart a distance approximately equal to the distance between carriage side walls 402 and 403. Likewise, the bottom edge portions 421 and 422 of lamp module side walls 416 and 417 are likewise spaced apart approximately the same distance as the spacing between front end wall 404 (FIG. 19) and intermediate wall 420. As a result, when the lamp module 410 is inserted downwardly atop the carriage to align the bottom open end of the lamp module with opening 408 of the carriage, the side walls and end walls are frictionally engaged by side walls 402 and 403 and walls 404 and 420 thereby holding the lamp module in place until upward force is applied to the lamp module handle 418. A plurality of ultraviolet lamps 423 have opposite ends mounted to walls 414 and 415 of lamp module 410 (FIG. 24). In the embodiment depicted in the drawing, a total of four ultraviolet lamps are mounted within the lamp module. Electrical connectors are mounted to walls 414 and 415 and project inwardly holding the proximal and distal ends of the lamps and electrically connecting the lamps to a source of electrical energy.

Lamp modules similar to lamp modules 410 and 411 are commercially available. For example, American Ultraviolet having an address of 212 South Mount Zion Road, Lebanon, Ind. 46052 markets a Closed End (CE) Reflector Germicidal Fixture with UV Lamps under Model Number CE-10-4SL. The American Ultraviolet fixtures are designed for general surface sterilization surfaces with up to four lamps per fixture and available as a free standing fixture.

A pair of mounts 470 and 471 are mounted respectively to end walls 414 and 415 of the ultraviolet lamp module. Mounts 470 and 471 are commercially available. For example, such mounts are available from American Ultraviolet with the germicidal fixture previously described. Each mount 470 and 471 includes female sockets into which the male pins at the opposite ends of the ultraviolet lamp extend thereby making an electrical connection while providing first and second mounts for holding the proximal ends and distal ends of the lamps.

Ultraviolet lamp module 411 is identical to lamp module 410 with exception that lamp module 411 is not provided with handle 18 and instead, a pair of upwardly extending flanges 460 (FIG. 17) are provided for wrapping an electrical cord thereon. Lamp module 410 and 411 are each provided with a lamp indicator and have a meter to show whether the lamps are powered on and the length of time the lamps have been powered. Further, a safety switch may be provided on handle 407 which must be moved before electrical energy is routed to the UV lamps.

A cover 430 (FIG. 21) has a top wall 431 connected to a pair of side walls 432 and 433 and a front wall 434. Side walls 432 and 433 are pivotally mounted by conventional fastening devices 435 to the side walls 402 and 403 of the carriage. A handle 436 is mounted atop wall 431 allowing the user to pull upwardly and pivot in a counterclockwise direction as viewed in FIG. 21 allowing access to the lamp modules 410 and 411 atop carriage bottom wall 406. Cover 430 has an open bottom allowing the cover to nest over the top of the lamp modules.

A commercially available Honda 1000 self-contained electrical generator 440 (FIG. 20) is fixedly mounted atop carriage bottom wall 406. The generator includes an internal combustion engine for generating the electrical energy routed to the two lamp modules.

A control box 450 (FIG. 20) is mounted atop bottom wall 406 of the carriage and is connectible via electrical cord 451 (FIG. 17) to either generator 440 or an external source of electrical energy such as provided via a conventional building wall plug. Cord 451 wraps around holders 452 mounted to handle 407. Cord 451 extends from control box 450 around handles 452 and has a conventional male plug 453 (FIG. 20) that may be inserted into the female connector provided on the generator or wall plug located remotely from the carriage. In the event the UV sterilization unit is to be used outdoors to sterilize a field and other objects, end 453 of the electrical cord is plugged into electrical generator 440. In the event the UV sterilization unit is to be used to sterilize objects within a building, then end 453 may be connected to the standard outlet providing electrical energy within the building. The lamp module 410 may then be removed from the carriage and carried to the object to be sterilized.

Figure 22:
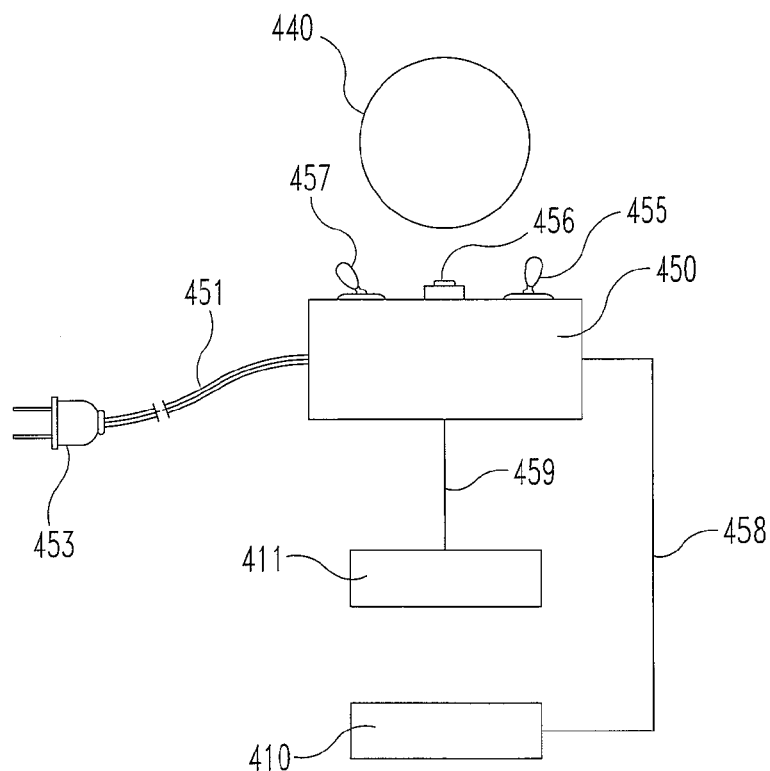
FIG. 22 is a schematic block diagram of the unit of FIG. 17.
Figure 23:
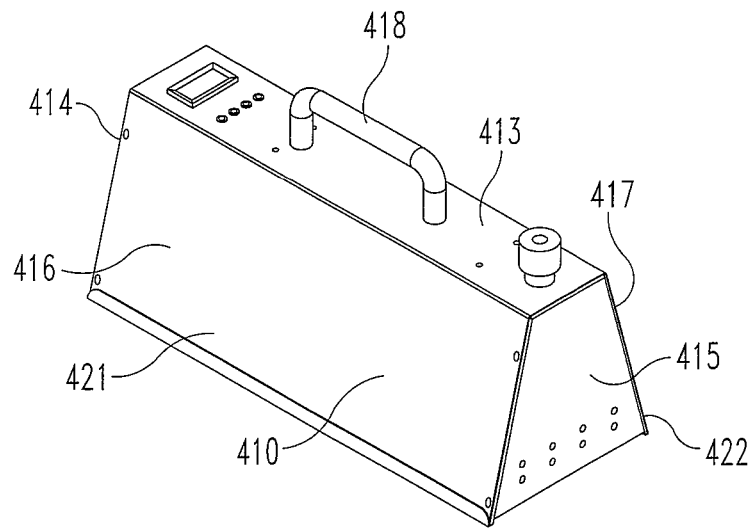
FIG. 23 is an enlarged perspective view of one of the lamp modules.

Control box 450 (FIG. 22) includes an indicator 455 that lights whenever electrical energy is provided to the control box. A conventional circuit breaker 456 automatically interrupts the power in case of a short, unacceptable spikes in electrical energy, or other undesirable events. A two position toggle switch 457 is used to control the flow of electrical energy to the ultraviolet lamp modules 410 and 411. In one position, the electrical energy provided by control box 450 is routed both to lamp module 410 and 411. For example, if the UV sterilization unit is to be used in sterilizing a turf field, then optimum performance is achieved by powering both UV ultraviolet lamps modules. In a second position of toggle switch 457, only ultraviolet lamp module 410 is connected to the electrical energy. In such a case, the lamp module 410 is removed from the carriage and moved from the carriage to the object to be sterilized. In this latter case, UV ultraviolet lamp module 411 is not connected to source of electrical energy. Ultraviolet lamp module 410 is connected to control box 450 by a conventional electrical cord 458 (FIG. 22). Likewise, ultraviolet lamp module 411 is connected to control box 450 by a conventional electrical cord 459. Excellent results have been obtained by using cord 458 of approximately 25 feet in length enabling the lamp module to be carried remotely from the carriage. Cord 458 may be wound around a pair of upwardly extending brackets 460 (FIG. 17) mounted to the top wall of lamp module 411.

The mobile UV sterilization unit 400 is connectable to an internally generated source of electrical energy such as provided by generator 440 and an externally generated source of electrical energy such as a conventional electrical wall outlet located within a building depending upon whether the sterilization unit is to be used outside or inside a building. The handle 407 provides a guide for directing the carriage across a field or other supporting surface as the user pushes on the handle. The two lamp modules 410 and 411 provide the ultraviolet light necessary to sterilize the surface located there below. Lamp module 410 has a first position removably located atop the carriage frame when the carriage is moved across a surface to be sterilized and a second position located remotely from the frame when the surface to be sterilized is located remotely from the carriage such as in a locker room, weight room, shower room or gymnasium. The ultraviolet lamps mounted within each lamp module housing are removable to allow for replacement of the defective bulbs. The control box previously described is selectively connectible to either the generator or the external source of energy.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, the vehicle and method described for sterilizing turf fields or sports fields it being understood that such includes not only soccer/football/lacrosse/baseball fields but also golf courses and any field having artificial or living turf susceptible to contamination.

What is claimed is:

1. A mobile UV Sterilization Unit connectable to an internally generated source of electrical energy and an externally generated source of electrical energy to destroy infectious material located on a surface comprising:
    a wheeled carriage having a frame with wheels depending therefrom and a device attached thereto to guide the carriage across a surface;
    a first portable lamp module having a first position removably located on said frame when said carriage is moved across a surface to be sterilized and a second position located remotely from said frame when the surface to be sterilized is located remotely from said carriage, said module has a lamp housing with a first housing open bottom;
    a first set of ultraviolet lamps removably mountable in said lamp housing and positioned to shine downwardly through said open bottom of said housing to shine against a surface to be sterilized, said lamps having proximal ends and distal ends;
    a control on said frame selectively connectable to an internally generated source of electrical energy on said frame and an externally generated source of electrical energy located remotely from said frame, said control connected to said lamps when said module is in said first position and said second position providing electrical energy to said lamps;
    first mounts receiving said proximal ends of said lamps and supporting said lamps in said housing;
    second mounts receiving said distal ends of said lamps and supporting said lamps in said housing;
    a second lamp module located on said frame when said carriage is moved across a surface to be sterilized, said second lamp module having a second lamp housing having an second housing open bottom;
a second set of ultraviolet lamps removably mountable in said second lamp housing and positioned to shine downwardly through said second housing open bottom to shine against a surface to be sterilized, said lamps having second proximal ends and second distal ends;
third mounts receiving said second proximal ends of said second set of ultraviolet lamps and supporting said second set of ultraviolet lamps in said second lamp housing; and,
fourth mounts receiving said second distal ends of said second set of ultraviolet lamps and supporting said second set of ultraviolet lamps in said second lamp housing with said second set of ultraviolet lamps connected to said internal electrical energy source; and wherein said first portable lamp housing has a first length and a first width, said frame includes a pair of side walls spaced apart a distance approximately equal to said first length and at pair of cross walls extending between side walls approximately equal to said width so said first portable lamp housing being forced in between said side walls and cross walls which is releasable and frictionally held on said frame, said first portable lamp housing, has a handle thereon for grasping to exert upwardly lifting force when moving said first portable lamp housing apart from said side walls and cross walls.

2. The mobile UV Sterilization Unit of claim 1 wherein said frame has a frame open bottom aligned with the first housing open bottom to allow said lamps to shine therethrough when said housing is in said first position.

3. The mobile UV Sterilization Unit of claim 1 and further comprising:
a cover mounted to said frame normally covering said first lamp module and said second lamp module but movable to uncover same.

4. The mobile UV Sterilization Unit of claim 1 and further comprising:
an electrical power cord connected to said first lamp module and connectable to an internally generated source of electrical energy and an externally generated source of electrical energy.

5. The mobile Sterilization Unit of claim 1 wherein:
said internally generated source of electrical energy includes a electrical generator mounted on said frame, said control having one position routing electrical energy from said generator or said externally generated source of electrical energy to said first, set of ultraviolet lamps and said second set of ultraviolet lamps and another position routing, electrical energy only to said first set of ultraviolet lamps.

6. The mobile UV Sterilization Unit of claim 1 wherein said carriage has a back end with said device extending outwardly therefrom with said device shaped to receive pushing force to manually move the carriage across the surface to be sterilized.

7. An ultraviolet sterilizer for sterilizing a field and objects remotely located from the field comprising:
a frame with wheels depending therefrom to support the frame on a field to be sterilized as said frame is moved across the field;
a first housing with first ultraviolet lamps mounted thereto with the housing being removably mounted to said frame and movable from a field sterilizing position located on said frame orienting said lamps to shine downwardly toward the field to be sterilized and a remote position apart from front said frame orienting said lamps to shine against objects remotely located from said field;
a second housing with second ultraviolet lamps mounted thereto with the second housing being mounted in a stationary position on said frame orienting said second ultraviolet lamps to shine downwardly toward the field to be sterilized;
a cover mounted to said frame normally covering and containing said first housing and said second housing but movable to uncover same and allow removal of said first housing and said second housing from said frame;
a source of electrical energy to direct electrical energy to both said first lamps and said second lamps when said field sterilizing position and to only said first lamps when said first housing is removed from and located remotely relative to said frame; and,
mounts on said frame to hold said first lamps and said second lamps on said frame; and wherein:
said first housing when located on said frame and connected to said source of electrical energy selectively receives electrical energy therefrom and when located remotely from said carriage can receive electrical energy from said source obtained remotely from said frame.

8. The ultraviolet sterilizer of claim 7 wherein:
said, frame includes a frame bottom wall, side walls and end walls with said first housing and said second housing positioned atop said frame bottom wall and between said side walls and end walls, said frame bottom wall is open and aligned with said first housing and second housing to allow ultraviolet light from said first ultraviolet lamps and said second ultraviolet lamps to shine therethrough.

9. The ultraviolet sterilizer of claim 7 wherein said source of electrical energy source includes an electrical generator mounted on said frame and connectable to said first ultraviolet lamps and said second ultraviolet lamps to route electrical energy from said generator thereto.

10. A mobile UV Sterilization Unit connectable to an internally generated source of electrical energy and an externally generated source of electrical energy to destroy infectious material located on a surface comprising:
a wheeled carriage having a frame with wheels depending therefrom and a device attached thereto to guide the carriage across a surface;
a pair of lamp modules with the one of the lamp modules having a first position removably located on said frame when said carriage is moved across a surface to be sterilized and a second position located remotely from said frame when the surface to be sterilized is located remotely from said carriage, said lamp modules have lamp housings with lengths, widths and open bottoms;
ultraviolet lamps removably mountable in said lamp housings and positioned to shine downwardly through said open bottoms of said housings to shine against a surface to be sterilized, said lamps having proximal ends and distal ends;
a control on said frame selectively connectable to an internally generated source of electrical energy on said frame and an externally generated source of electrical energy located remotely from said frame, said control connected to said lamps both when in said first position and said second position providing electrical energy to said lamps;
mounts receiving said proximal ends and said distal ends of said lamps and supporting said lamps in said housings; and wherein:

said frame includes a pair of side walls spaced apart a distance approximately equal to the length of a housing and a pair of cross walls spaced apart a distance approximately equal to the width of the housing so the housing is forced in between said side walls and cross walls and releasably and frictionally held on said frame.

11. The mobile UV Sterilization Unit of claim 10 and further comprising:

a cover mounted to said frame normally covering and containing said lamp modules but movable to uncover same and allow removal of said lamp modules from said frame.

12. The mobile UV Sterilization Unit of claim 11 wherein:

said internally generated source of electrical energy includes an electrical generator mounted on said frame.

* * * * *